(12) United States Patent
Suzuki (10) Patent No.: US 7,309,129 B2
(45) Date of Patent: Dec. 18, 2007

(54) PERIMETER

(75) Inventor: Naoto Suzuki, Aichi (JP)

(73) Assignee: Nidek Co., Ltd., Aichi (JP)

( * ) Notice: Subject to any disclaimer, the term of this patent is extended or adjusted under 35 U.S.C. 154(b) by 489 days.

(21) Appl. No.: 10/953,419

(22) Filed: Sep. 30, 2004

(65) Prior Publication Data
US 2005/0068498 A1    Mar. 31, 2005

(30) Foreign Application Priority Data
Sep. 30, 2003    (JP)    ............. P.2003-340141

(51) Int. Cl.
*A61B 3/02* (2006.01)
(52) U.S. Cl. ...................... 351/224; 351/206
(58) Field of Classification Search ................ 351/205, 351/206, 210, 222–224
See application file for complete search history.

(56) References Cited

U.S. PATENT DOCUMENTS

| | | | |
|---|---|---|---|
| 4,279,478 A * | 7/1981 | Matsumura | ................. 351/206 |
| 5,037,194 A * | 8/1991 | Kohayakawa et al. | ...... 351/224 |
| 5,323,194 A | 6/1994 | Campbell et al. | |
| 5,463,431 A | 10/1995 | Suzuki et al. | |
| 6,053,865 A | 4/2000 | Sugiyama et al. | |
| 6,705,726 B2 | 3/2004 | Tanassi et al. | |
| 2003/0157464 A1 | 8/2003 | Tanassi et al. | |

FOREIGN PATENT DOCUMENTS

| | | |
|---|---|---|
| JP | 6-54804 A | 3/1994 |
| WO | WO 93/18702 A1 | 9/1993 |

* cited by examiner

*Primary Examiner*—Huy Mai
(74) *Attorney, Agent, or Firm*—Sughrue Mion, PLLC (57) ABSTRACT

A perimeter for examining a visual field of an eye of a patient, includes: a presentation unit, which presents an examination target at each of various positions around an eye fixation point to which the patient's eye is visually fixed; a position determination unit, which determines at least one of positions of an optic pappila, a central fovea and a macula lutea on a fundus of the patient's eye; and a control unit, which determines a running state of a nerve fiber bundle on the fundus based on the determined position, and which controls the presentation unit to present and move the examination target based on the determined running state of the nerve fiber bundle.

12 Claims, 6 Drawing Sheets

PERIMETER

BACKGROUND OF THE INVENTION

The present invention relates to a perimeter for examining (measuring) the visual field (field of view) of a patient's eye.

A static perimeter and a dynamic perimeter are known as a perimeter for examining the visual field of a patient's eye. The static perimeter sequentially presents an examination target at each of examination points on the fundus of the patient's eye, and examines the visual field of the patient's eye based on patient's responses as to whether or not the patient can visually recognize the examination target at each point. The dynamic perimeter presents an examination target having a predetermined luminance on the fundus of the patient's eye, while moving the examination target thereon, and examines the visual field of the patient based on patient's responses of visual recognition.

The dynamic perimeter is a very effective device for understanding a two-dimensional sensitivity distribution of the visual field of the patient. However, the dynamic perimetry requires skill and experience, and takes long time for examination.

SUMMARY OF THE INVENTION

It is one objective of the present invention to provide a perimeter that can reduce the time required for a dynamic perimetry, and that can provide accurate results.

In order to solve the aforesaid object, the invention is characterized by having the following arrangement.

(1) A perimeter for examining a visual field of an eye of a patient, comprising:

a presentation unit, which presents an examination target at each of various positions around an eye fixation point to which the patient's eye is visually fixed;

a position determination unit, which determines at least one of positions of an optic pappila, a central fovea and a macula lutea on a fundus of the patient's eye; and a control unit, which determines a running state of a nerve fiber bundle on the fundus based on the determined position, and which controls the presentation unit to present and move the examination target based on the determined running state of the nerve fiber bundle.

(2) A perimeter according to (1), wherein the control unit controls the presentation unit to move the presented examination target along the determined running state.

(3) A perimeter according to (1), wherein the control unit controls the presentation unit to move the presented examination target in a direction perpendicular to the determined running state.

(4) A perimeter according to (1), further comprising:

an observation unit, which includes an image pickup device and a display unit, and which displays, on the display unit, a fundus observation image of the patient's eye obtained by the image pickup device, wherein the position determination unit determines the positions of the optic pappila and the central fovea or the macula lutea, on the displayed fundus observation image, and wherein the control unit determines the running state of the nerve fiber bundle on the fundus observation image based on the determined positions.

(5) A perimeter according to (4), wherein the control unit includes:

a storage unit, which stores fundus image model data that includes a typical optic papilla and a typical central fovea or a typical macula lutea, and that indicates a typical running state of a nerve fiber bundle, wherein the control unit analyzes a correlation between the fundus observation image and the fundus image model data based on the determined positions to determine the running state of the nerve fiber bundle on the fundus observation image.

(6) A perimeter according to (4), wherein the control unit displays the determined running state of the nerve fiber bundle on the display unit, while superimposing the determined running state onto the fundus observation image.

(7) A perimeter according to (1), further comprising:

a photographing unit which includes an image pickup device, and which photographs the fundus of the patient's eye.

(8) A perimeter according to (7), wherein the eye fixation point for perimetry is used commonly as an eye fixation point for photographing the fundus.

(9) A perimeter for examining a visual field of an eye of a patient, comprising:

a presentation unit, which presents an examination target at each of various position around an eye fixation point to which the patient's eye is visually fixed;

an observation unit, which has an image pickup device and a display unit, and which displays, on the display unit, a fundus observation image of the patient's eye obtained by the image pickup device;

a position determination unit, which determines positions of an optic papilla and a central fovea or a macula lutea on the displayed fundus observation image; and a control unit, which determines a running state of a nerve fiber bundle on the fundus observation image based on the determined positions, and which displays, on the display unit, the determined running state of the nerve fiber bundle, while superimposing the determined running state onto the fundus observation image.

(10) A perimeter according to (9), wherein the control unit includes:

a storage unit, which stores fundus image model data that includes a typical optic papilla and a typical central fovea or a typical macula lutea, and that indicates a typical running state of a nerve fiber bundle, wherein the control unit analyzes a correlation between the fundus observation image and the fundus image model data based on the determined positions to determine the running state of the nerve fiber bundle on the fundus observation image.

(11) A perimeter according to (9), further comprising: a photographing unit which has an image pickup device, and which photographs the fundus of the patient's eye.

(12) A perimeter according to (11), wherein the eye fixation target for perimetry is used commonly as an eye fixation target for photographing the fundus.

(13) A perimeter for examining a visual field of an eye of a patient, comprising:

a presentation unit, which presents an examination target at each of various positions around an eye fixation point to which the patient's eye is visually fixed;

an observation unit, which has an image pickup device and a display unit, and which displays, on the display unit, a fundus observation image of the patient's eye obtained by the image pickup device; and a photographing unit, which has an image pickup device and which photographs a fundus of the patient's eye, wherein the eye fixation point for perimetry is used commonly as an eye fixation point for photographing the fundus.

DETAILED DESCRIPTION OF PREFERRED EMBODIMENTS

Figure 1:
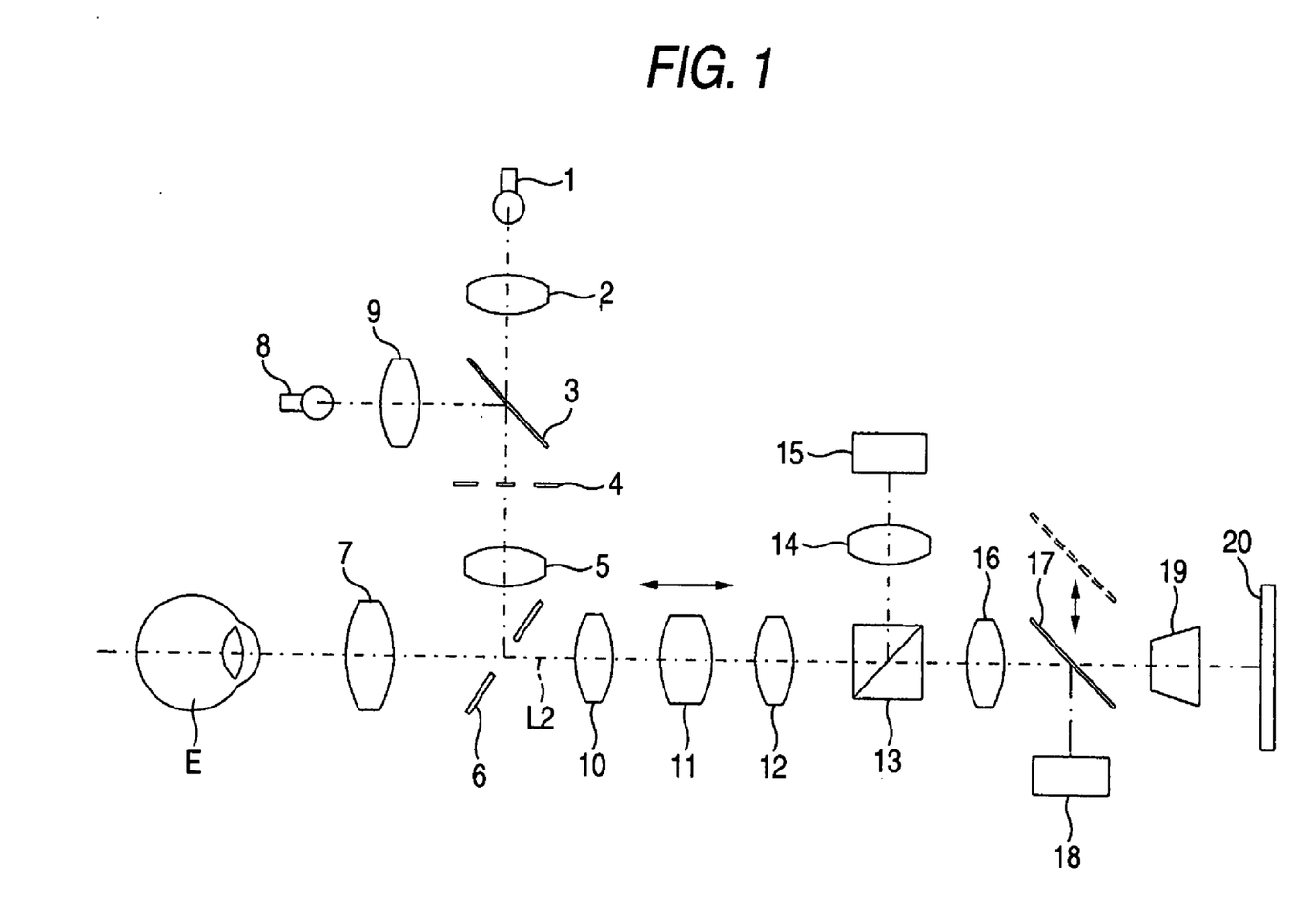
FIG. 1 is a schematic structural diagram as to an optical system of an ophthalmic apparatus according to an embodiment of the present invention.
Figure 2:
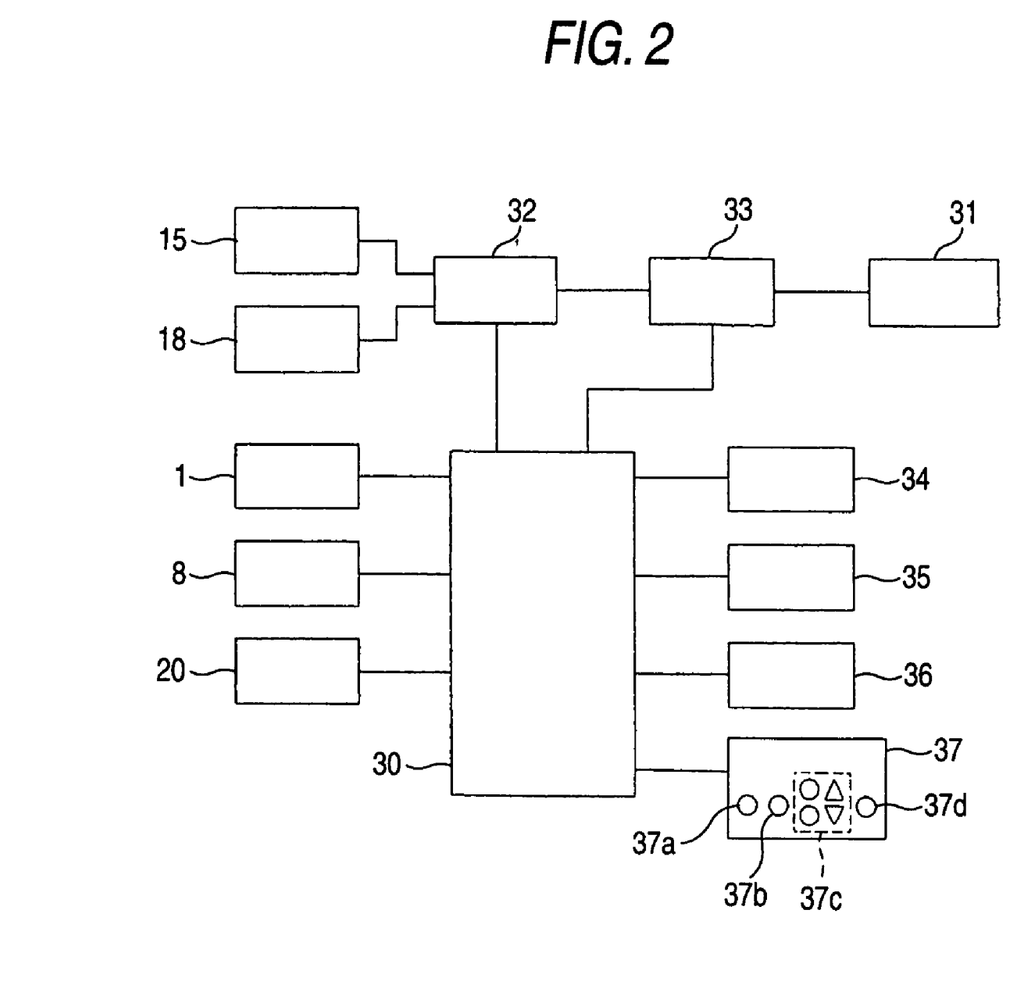
FIG. 2 is a schematic block diagram for showing a control system of the ophthalmic apparatus.

Referring now to drawings, an embodiment of the present invention will be described. FIG. 1 is a schematic structural diagram showing an optical system of an ophthalmic apparatus according to this embodiment, which has a fundus camera function and a perimeter function. FIG. 2 is a schematic block diagram of a control system of this ophthalmic apparatus.

In FIG. 1, symbol "E" shows a patient's eye, i.e. an eye to be examined. Light emitted from an observation-purpose illumination light source 1 such as a halogen lamp is converted into infrared light by an infrared transmission filter (not shown) that illuminates a slit plate 4 having a ring slit 4a via a condenser lens 2 and a dichroic mirror (cold mirror) 3. The light (ring slit light) which has passed through the ring slit 4a forms an intermediate image in the vicinity of an aperture (opening) of a hole mirror 6 via a relay lens 5, and also, is reflected by a peripheral plane of the mirror 6 around the aperture. The light reflected by the mirror 6 is once focused in the vicinity of a pupil of the eye E by an objective lens 7, and thereafter, is diffused so as to illuminate a fundus "Ef" of the eye E uniformly. The mirror 3 has such a wavelength selection characteristic as to reflect visible light thereby, while passing infrared light therethrough. On the other hand, visible illumination light emitted from a photographing-purpose (imaging-purpose) illumination light source 8 such as a xenon flash lamp is traveled via another condenser lens 9, and the mirror 3, and is transmitted via the optical elements from the slit plate 4 to the lens 7 to illuminate the fundus Ef of the eye E similarly to the infrared illumination light. An illumination optical system (namely, both observation-purpose illumination optical system and photographing-purpose illumination optical system) is formed by this construction. In addition, instead of the light source 1 and the infrared transmission filter, an infrared illumination light source may be alternatively employed.

The infrared reflection light reflected from the fundus Ef of the eye E is traveled through the lens 7, the mirror 6, lenses 10, 11, 12, a dichroic mirror 13, and a lens 14 to be focused onto a light receiving plane of an observation-purpose camera 15 having a sensitivity in an infrared region. The mirror 13 has such a wavelength selection characteristic as to reflect infrared light thereby, while passing visible light therethrough. The lens 11 is movable in an optical axis direction to put the fundus Ef of the eye E and the light receiving plane of the camera 15 into a conjugate positional relationship. An observation optical system is constructed in this fashion.

On the other hand, visible reflection light reflected from the fundus Ef of the eye Eis traveled via the optical elements from the lens 7 to the mirror similarly to the infrared reflection light, and is transmitted via a lens 16 and a reflection mirror 17 to be focused onto a light receiving plane of a photographing-purpose (imaging-purpose) camera 18 having a sensitivity in a visible region. The light receiving plane of the camera 18 and the light receiving plane of the camera are positioned to have a conjugate positional relationship. A photographing (imaging) optical system is formed in this manner.

The optical axis L1 of the illumination optical system (lenses 2, 5, 9) and an optical axis L2 of the observation optical system and the photographing optical system (lenses 10, 11, 12, 14, 16) are coaxial with respect to an optical axis of the lens 7.

The optical system used in the perimetry is arranged by commonly using the optical elements from the lens 7 to the lens 16 of the photographing optical system, and by employing a reducing lens 19 and a liquid crystal display (LCD) 20 for presenting an examination target (stimulation target). The lens 19 is employed so as to focus an entire image of the target presenting region of the LCD 20 onto the light receiving plane of the camera 15 in combination with an image of the fundus Ef of the eye E. When the perimetry is carried out (when the examination target is presented), the mirror 17 is moved out of the optical path. The examination target presented on the LCD 20 is projected via the optical elements from the lens 19 to the lens 7 onto the fundus Ef of the eye E. An eye fixation target (eye fixation point) having a cross shape is formed on a center (on the optical axis "L2") of the LCD 20. As to the examination target, a presenting position thereof, luminance thereof, and a dimension thereof can be varied.

The light source 1, the light source 8, the LCD 20, an image processing unit 32, a memory 34, a response button 35, an input device 36 such as a mouse, an operation unit 37 equipped with various sorts of switches and keys, and the like are connected to a control unit 30. This control unit 30 is employed so as to drive/control an entire system of the ophthalmic apparatus. The button 35 is pushed (manipulated) when a patient, i.e. a person under examination, can visually recognize a presented examination target during perimetry. The input device 36 is used to designate, on the monitor 31, a presenting position of the examination target and a direction in which the examination target is moved during dynamic perimetry. The operation unit 37 includes: a photographing (image pickup) switch 37a; a mode switching switch 37b, for changing a fundus photographing mode and a perimetry mode; a group of setup keys 37c, used to set the presenting position, luminance, dimension and the like of the examination target; and a detailed examination switch 37d, used for displaying a superimposed image in which a schematic diagram showing a running state of the nerve fiber bundle is superimposed on an observation image of the fundus Ef.

The image processing unit 32 performs an image processing operation such as a color tone correction with respect to images obtained by the camera 15 and the camera 18. The image switching unit 33 switches an observation image in the form of time-varying image obtained by the camera 15 and a photographed image in the form of a still image obtained by the camera 18 so that any one of the observation image and the photographed image is displayed on the monitor 31. The memory 34 stores therein the photographed image obtained by the camera 18 and response information (subjective information) obtained from the patient during perimetry. The memory 34 also stores therein fundus image model data that includes the papilla disc and the central fovea (or the macula lutea), and that indicates the running state of the nerve fiber bundle.

Figure 3:
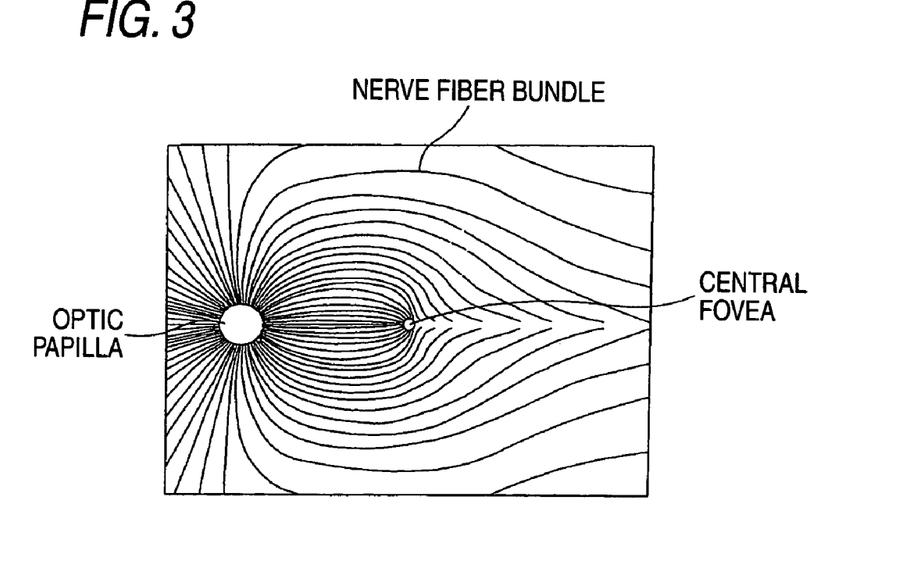
FIG. 3 is a diagram showing an example of fundus image model data in which the running state of a nerve fiber bundle is indicated.

FIG. 3 is a diagram showing an example of the fundus image model data stored in the memory 34. The fundus image model data is a schematic diagram data showing the running state of the nerve fiber bundle around the optic papilla and the central fovea (or the macula lutea) on the fundus of a typical and healthy eye, and is employed for dynamic perimetry, which will be described later. Although the fundus of the eye actually has a larger number of nerve fiber bundle, it is unnecessary for the fundus image model data to include all of the nerve fiber bundle. That is, it is sufficient for the fundus image model data to include an appropriate number of nerve fiber bundle, along which the examination target presented onto the eye E (fundus Ef) can be moved during perimetry that will be described later.

A description is made of operations as to the ophthalmic apparatus equipped with the above-described arrangement.

An examiner or doctor (hereafter referred to simply as the doctor) turns on the light source 1 to illuminate the fundus Ef of the eye E with the infrared illumination light, and observes an image of the fundus Ef displayed on the monitor 31. Next, the doctor moves the lens 11 in the optical axis direction so that the image of the fundus Ef is clearly displayed on the monitor 31. The control unit 30 moves the mirror 17 so that the mirror 17 is out of the optical axis L2 during the observation of the fundus Ef (with the exception of photographing the fundus Ef). The control unit 30 displays an eye fixation target at a center of the LCD 20.

The doctor depresses (manipulates) the switch 37a to obtain an image of the fundus Ef. When the switch 37a is depressed, the control unit 30 turns on the light source 18 to illuminate the fundus Ef with visible illumination light, and positions the mirror 17 on the light axis L2. Accordingly, an image of the fundus Ef is obtained by the camera 18. When the image of the fundus Ef is obtained by the camera 18 (or the switch 37a is depressed), the control unit 30 switches, via the image switching unit 33, to switch a display on the monitor 31 from the observation image obtained by the camera 15 to the photographed image obtained by the camera 18. At this time, the image processing unit 32 performs appropriate image correction, such as tone correction, onto the image of the fundus Ef obtained by the camera 18 so that the processed color image of the fundus Ef is displayed on the monitor 31. The doctor confirms the displayed image of the fundus Ef, and then depresses (manipulates) a print switch (not shown) of the operation unit 37. The image of the fundus Ef thus obtained (displayed) is printed by a printer (not shown), and the fundus Ef is examined. In addition, the position of the eye fixation target displayed on the LCD 20 may be changeable, and the image pickup area for the fundus Ef may be variable.

Following this, the doctor manipulates the switch 37b to change the fundus photographing mode to the perimetry mode, and performs a dynamic perimetry, while referring to the observation image of the fundus Ef on the monitor 31 and the outputted (printed) image of the fundus Ef. When the mode is changed to the perimetry mode, the control unit 30 removes the mirror 17 out of the light axis L2, and switches a display on the monitor 31 from the photographed image obtained by the camera 18 to the observation image obtained by the camera 15.

Figure 4:
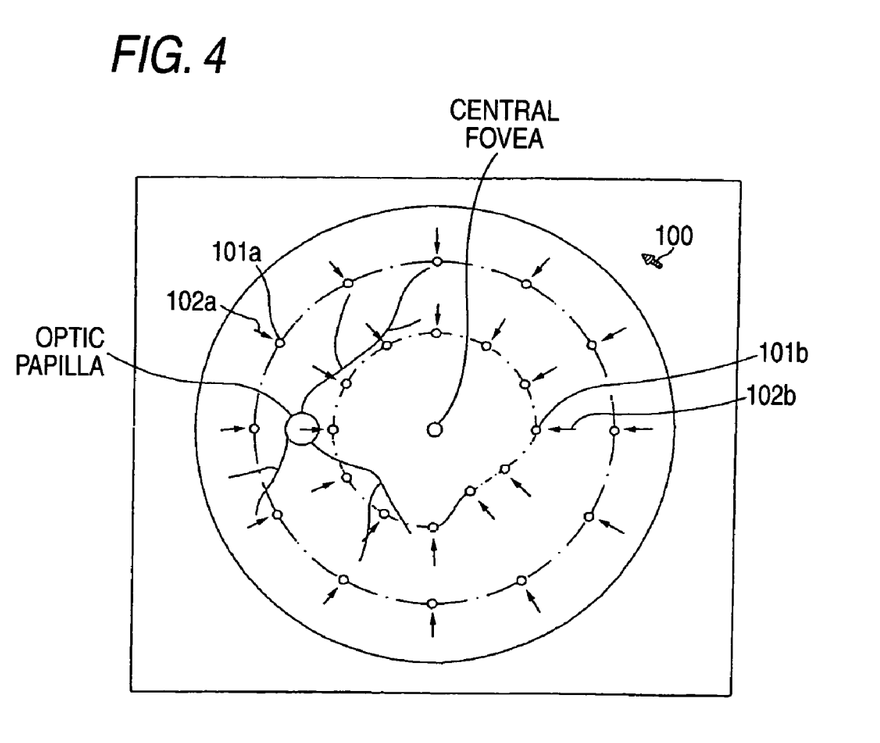
FIG. 4 is a diagram showing an example of a fundus observation image during perimetry.

FIG. 4 is a diagram showing an example of the observation image 110 of the fundus Ef during perimetry. The doctor manipulates the group of keys 37c to designate the dimension (shape) of the examination target and the luminance A thereof, and then operates the input device 36 to move a cursor 100 displayed on the observation image 110 of the fundus Ef, to thereby designate a start position at which the examination target is to be initially presented on the fundus Ef and from which the examination is to be moved. In this embodiment, this start position, i.e. the moving and presentation start position, is designated on the circumferential edge of the observation image 110 of the fundus Ef displayed on the monitor 31.

After the moving and presentation start position of the examination target is designated, the control unit 30 presents the examination target at such a predetermined position on the LCD 20 as to correspond to the designated moving and presentation start position. Further, the control unit 30 moves the examination target at a predetermined speed (for example, 5° per second) toward the center of the LCD 20. Accordingly, the examination target is presented and moved from the peripheral portion of the fundus Ef toward the central fovea (the macula lutea).

When the patient can visually recognize the examination target, the patient depresses the button 35 to notify the doctor and the apparatus of the fact that the examination target can be visually recognized. Upon the depression of the button 35, the control unit 30 turns off the presented examination target on the LCD 20 (stops the presentation of the examination target). Furthermore, as shown in FIG. 4, the control unit 30 uses the image processing unit 32 to display (form) a target mark 101a at such a position on the observation image 110 of the fundus Ef as to correspond to the examination target presentation position (the visually recognized position) at the time when the button 35 is depressed. That is to say, the position of the target mark 101a corresponds to the visually recognized position designated by the depression of the button 35 in this embodiment. Moreover, an arrow 102a indicating the direction in which the examination target has been moved is also formed (displayed) adjacent to the target mark 101a.

In the same manner, an examination target having the same luminance A is presented and moved from each start position toward the central fovea in a respective direction so that the isopter for the luminance A (the contour line of sensitivity with respect to the luminance A) is obtained. In addition, response information received from the patient is stored in the memory 34 one by one.

Next, an examination target having luminance B, which is lower than the luminance A, is presented and moved toward the central fovea from the inside of the isopter for the luminance A so that an isopter for the luminance B is obtained in the similar manner as mentioned above. As shown in FIG. 4, a target mark 101b is displayed (formed) at such a position on the observation image 110 of the fundus Ef that corresponds to the examination target presentation position (the visually recognized position) of the luminance B. Further, an arrow 102b indicating the direction in which the examination target having the luminance B has been moved is also displayed (formed).

After the isopters for the respective luminance levels are formed, the visual field sensitivity at each position on the fundus Ef is further examined dynamically. Generally, the isopters are substantially concentrically formed about the central fovea; however, in case the visual field has been altered by glaucoma, for example, the isopters are not concentrically formed. Since the visual field impairment produced by glaucoma, such as isolated scotoma, bow-shaped scotoma or a nose-oriented stairway effect, is considered to be the result of a nerve fiber bundle disorder, and the progression of this impairment is developed along the line of the nerve fiber bundle. In this embodiment, therefore, after the isopters are roughly formed on the fundus, dynamic perimetry along the line of the nerve fiber bundle is performed for a portion (a deformed portion) in which the isopters are not concentrically formed, to thereby form more detailed isopters.

The doctor depresses (manipulates) the switch 37d, and thereafter moves the cursor 100 to designate positions of the optic papilla and the central fovea (or the macula lutea) on the observation image 110 of the fundus Ef displayed on the monitor 31. After each of these positions is designated, the control unit 30 retrieves the fundus image model data (see FIG. 3) from the memory 34. Thereafter, based on positioning information for the two positions designated by the cursor 100, the control unit 30 measures the distance between the two positions, and enlarges or reduces the schematic diagram produced using the fundus image model data, so that the distance between the optic papilla and the central fovea of the fundus image model data matches the distance between the two positions. Further, the control unit 30 displays the enlarged or reduced schematic diagram of the fundus image model data to be superimposed on the observation image 110 of the fundus Ef so that the optic papilla and the central fovea in the image of the fundus image model data are respectively aligned with the optic papilla and the central fovea in the observation image 110 of the fundus Ef.

Figure 5:
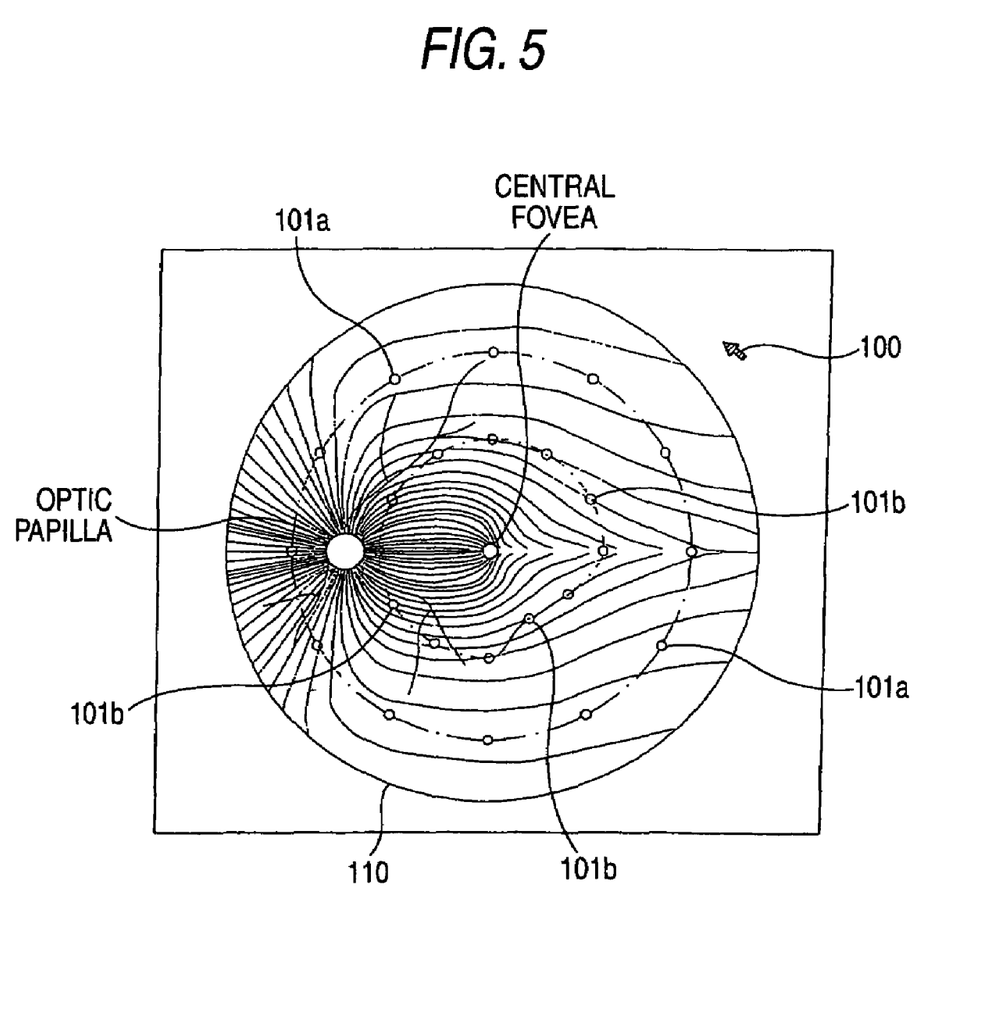
FIG. 5 is a diagram showing an example of a superimposed display in which a schematic diagram showing the running state of the nerve fiber bundle is superimposed on the fundus observation image.

FIG. 5 is a diagram showing an example of the superimposed display in which the schematic diagram produced using the fundus image model data is superimposed on the observation image 110 of the fundus Ef on the monitor 31. With this display, the doctor need only view the monitor 31 to easily confirm the running state of the nerve fiber bundle on the fundus.

Figure 6:
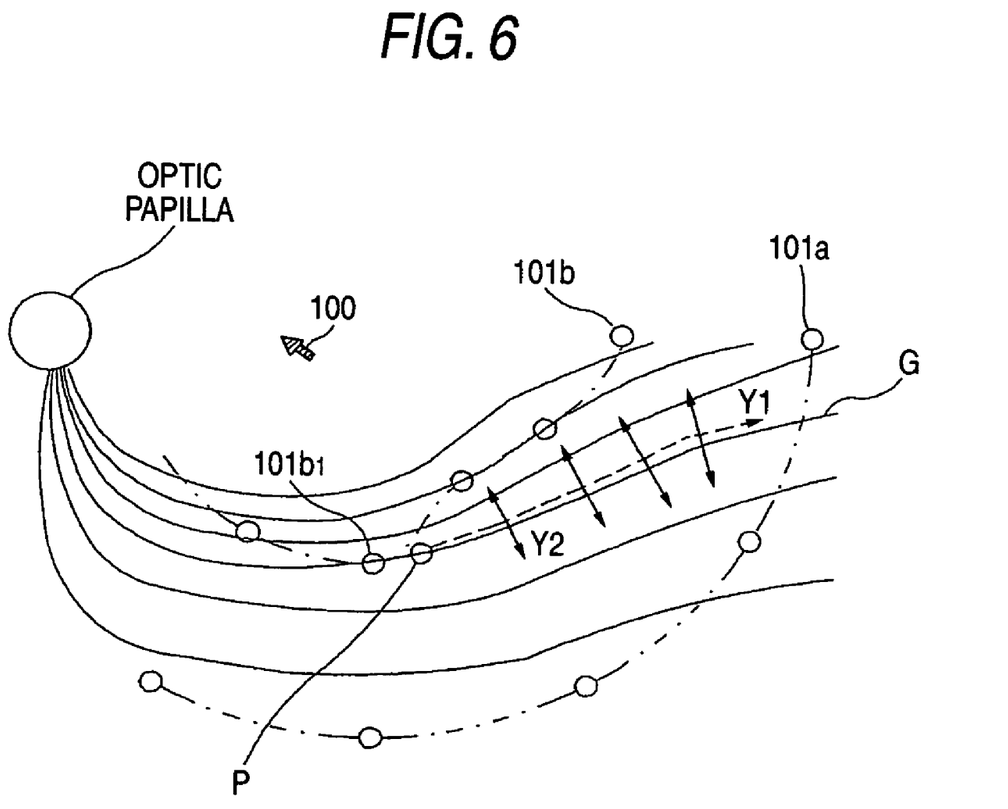
FIG. 6 is a partially enlarged diagram showing a deformed portion of an isopter.

As shown in FIG. 5, the isopters formed in this embodiment have a deformed portion, i.e. the lower right portion in the paper plane, in which the isopter formed by the target marks 101b (the isopter of the luminance B) is deformed. FIG. 6 is a partially enlarged diagram showing the deformed portion of the isopter in FIG. 5.

The doctor employs the cursor 100 to designate a moving and presentation start position P of an examination target again. In this embodiment, the examination target having luminance A is used, because the examination target having the luminance A is currently regarded as having been visually recognized by the patient in a region outside the isopter formed by the target marks 101b. Further, in this embodiment, the doctor designates, as the moving and presentation start position P, a position slightly outside a specific position (for example, an target mark 101b1) of the deformed portion of the isopter formed by the target marks 101b.

When the position P has been designated, the control unit 30 presents the examination target at the position P and moves the presented examination target therefrom at a predetermined speed along a line of a nerve fiber bundle G that runs through the position P in a direction toward the isopter formed by the target marks 101a (in the direction indicated by an arrow Y1 in FIG. 6).

The patient depresses the button 35 to transmit a response when the patient can visually recognize the presented examination target moved along the line of the nerve fiber bundle G. When the button 35 is depressed, the control unit 30 displays a target mark 101a at such a position on the observation image 110 of the fundus Ef that corresponds to the examination target presentation position (the visually recognized position) designated by depressing the button 35. Next, the doctor moves the cursor 100 to designate an arbitrary position on the nerve fiber bundle G along which the presented examination target has been moved. The control unit 30 presents an examination target at the designated arbitrary position on the nerve fiber bundle G, and moves the presented examination target from the designated arbitrary position in a direction perpendicular to the nerve fiber bundle G (in the direction indicated by an arrow Y2 in FIG. 6). The patient employs the button 35 to transmit a response of the visual recognition in the same manner as mentioned above, and the control unit 30 displays a target mark 101a based on this response.

Figure 7:
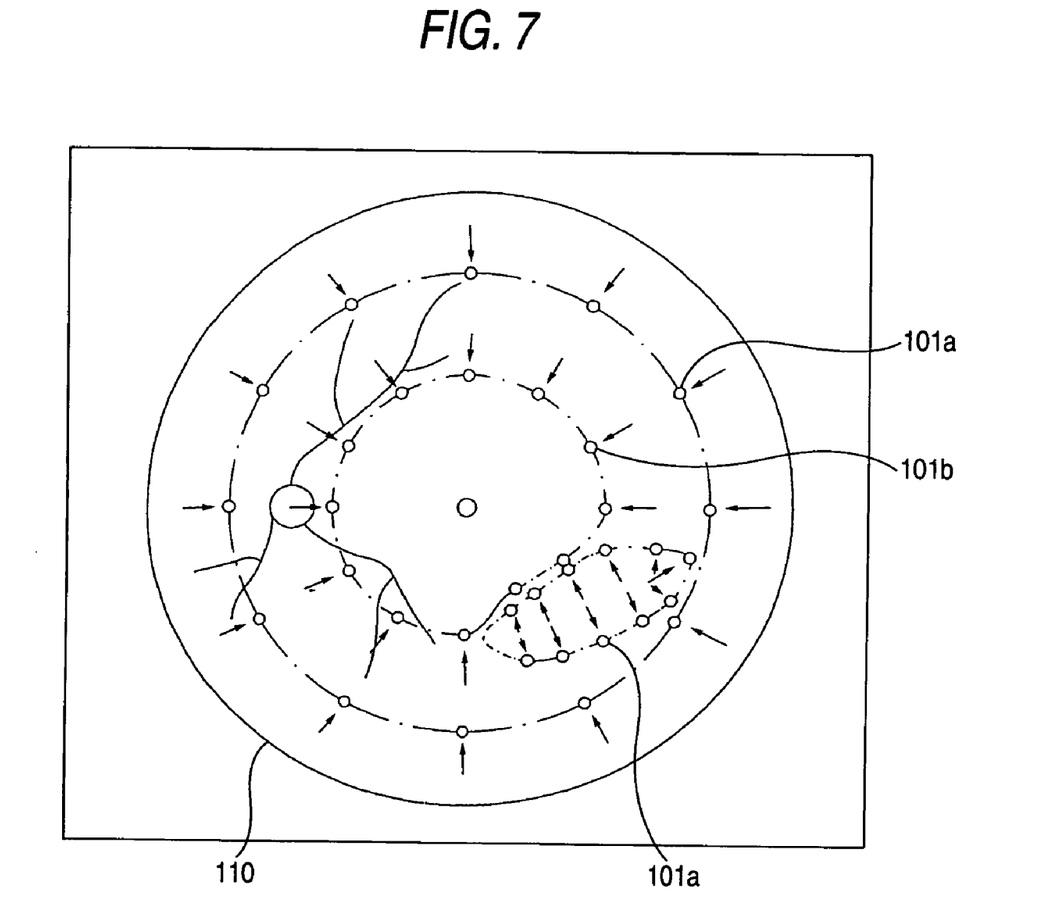
FIG. 7 is a diagram showing isopters that indicate detailed visual field sensitivity.

When all of the examination targets have been presented, the doctor depresses (manipulates) an end switch (not shown) of the operation unit 37. When the end switch is depressed, the control unit 30 erases the fundus image model data from the monitor 31, and displays the isopters that provide a more detailed representation of the visual field sensitivity as shown in FIG. 7.

As described above, according to the embodiment, since dynamic perimetry can be performed in accordance with the running state of the nerve fiber bundle, a scotoma can be easily found. As a result, compared with the conventional dynamic perimetry, the time required for examination can be reduced, and an accurate perimetry can be performed.

Although this embodiment has been described with reference to a case in which only the dynamic perimetry is performed, the present invention is not limited thereby, and can be applied to a case in which the examination is performed after the static perimetry is performed. Further, in designating the moving direction of the examination target, two positions may be entered as desired by using the input device 36 to designate the start position and the direction of movement.

Furthermore, in this embodiment, the distance between the optic papilla and the central fovea (or the macula lutea) of the fundus observation image is employed to superimpose, on the display, the fundus observation image and the schematic diagram showing the running state of the nerve fiber bundle of the fundus image model data. Instead of this distance, positioning data for the optic papilla and the central fovea (the macula lutea) of the fundus observation image may be employed to analyze the correlation between the fundus observation image and the fundus image model data, and to match the fundus observation image and the fundus image model data. For example, the coordinates of the optic papilla and the central fovea (the macula lutea) of the fundus observation image displayed on the monitor may be obtained, and the schematic diagram showing the running state of the nerve fiber bundle may be superimposed on the fundus observation image so that the optic papilla and the central fovea or the macula lutea) of the fundus image model data are positioned at the obtained coordinates.

What is claimed is:

1. A perimeter for examining a visual field of an eye of a patient, comprising:

a presentation unit, which presents an examination target at each of various positions around an eye fixation point to which the patient's eye is visually fixed;

a position determination unit, which determines at least one of positions of an optic papilla, a central fovea and a macula lutea on a fundus of the patient's eye; and a control unit, which determines a running state of a nerve fiber bundle on the fundus based on the determined position, and which controls the presentation unit to present and move the examination target based on the determined running state of the nerve fiber bundle.

2. A perimeter according to claim 1, wherein the control unit controls the presentation unit to move the presented examination target along the determined running state.

3. A perimeter according to claim 1, wherein the control unit controls the presentation unit to move the presented examination target in a direction perpendicular to the determined running state.

4. A perimeter according to claim 1, further comprising:

an observation unit, which includes an image pickup device and a display unit, and which displays, on the display unit, a fundus observation image of the patient's eye obtained by the image pickup device, wherein the position determination unit determines the positions of the optic papilla and the central fovea or the macula lutea, on the displayed fundus observation image, and wherein the control unit determines the running state of the nerve fiber bundle on the fundus observation image based on the determined positions.

5. A perimeter according to claim 4, wherein the control unit includes:

a storage unit, which stores fundus image model data that includes a typical optic papilla and a typical central fovea or a typical macula lutea, and that indicates a typical running state of a nerve fiber bundle, wherein the control unit analyzes a correlation between the fundus observation image and the fundus image model data based on the determined positions to determine the running state of the nerve fiber bundle on the fundus observation image.

6. A perimeter according to claim 4, wherein the control unit displays the determined running state of the nerve fiber bundle on the display unit, while superimposing the determined running state onto the fundus observation image.

7. A perimeter according to claim 1, further comprising:

a photographing unit which includes an image pickup device, and which photographs the fundus of the patient's eye.

8. A perimeter according to claim 7, wherein the eye fixation point for perimetry is used commonly as an eye fixation point for photographing the fundus.

9. A perirmeter for examining a visual field of an eye of a patient, comprising:

a presentation unit, which presents an examination target at each of various position around an eye fixation point to which the patients eye is visually fixed;

an observation unit, which has an image pickup device and a display unit, and which displays, on the display unit, a fundus observation image of the patients eye obtained by the image pickup device;

a position determination unit, which determines positions of an optic papilla and a central fovea or a macula lutea on the displayed fundus observation image; and a control unit, which determines a running state of a nerve fiber bundle on the fundus observation image based on the determined positions, and which displays, on the display unit, the determined running state of the nerve fiber bundle, while superimposing the determined running state onto the fundus observation image.

10. A perimeter according to claim 9, wherein the control unit includes:

a storage unit, which stores fundus image model data that includes a typical optic papilla and a typical central fovea or a typical macula lutea, and that indicates a typical running state of a nerve fiber bundle, wherein the control unit analyzes a correlation between the fundus observation image and the fundus image model data based on the determined positions to determine the running state of the nerve fiber bundle on the fundus observation image.

11. A perimeter according to claim 9, further comprising: a photographing unit which has an image pickup device, and which photographs the fundus of the patient's eye.

12. A perimeter according to claim 11, wherein the eye fixation target for perimetry is used commonly as an eye fixation target for photographing the fundus.

* * * * *